(12) United States Patent
Norsted

(10) Patent No.: US 10,632,274 B2
(45) Date of Patent: Apr. 28, 2020

(54) CPAP MASK ATTACHMENT SYSTEM

(71) Applicant: Jeffrey Norsted, Woodbury, MN (US)

(72) Inventor: Jeffrey Norsted, Woodbury, MN (US)

( * ) Notice: Subject to any disclaimer, the term of this patent is extended or adjusted under 35 U.S.C. 154(b) by 317 days.

(21) Appl. No.: 15/497,600

(22) Filed: Apr. 26, 2017

(65) Prior Publication Data

US 2017/0312470 A1 Nov. 2, 2017

Related U.S. Application Data

(60) Provisional application No. 62/329,051, filed on Apr. 28, 2016.

(51) Int. Cl.
*A61M 16/06* (2006.01)
*A61M 16/08* (2006.01)
*A61M 16/04* (2006.01)

(52) U.S. Cl.
CPC .... *A61M 16/0683* (2013.01); *A61M 16/0493* (2014.02); *A61M 16/0816* (2013.01)

(58) Field of Classification Search
CPC .............. A61M 16/00; A61M 16/0489; A61M 16/0493; A61M 16/06; A61M 16/0605; A61M 16/0611; A61M 16/0616; A61M 16/0622; A61M 16/0683; A61M 16/0816; A61M 15/0021; A61M 15/085; A61F 5/56; A61F 5/566; A61B 90/16
See application file for complete search history.

(56) References Cited

U.S. PATENT DOCUMENTS

| | | | |
|---|---|---|---|
| 5,537,994 A * | 7/1996 | Thornton | A61F 5/566 128/201.18 |
| 5,752,510 A | 5/1998 | Goldstein et al. | |
| 5,954,048 A * | 9/1999 | Thornton | A61F 5/566 128/201.18 |
| 5,983,892 A | 11/1999 | Thornton et al. | |
| 6,012,455 A | 1/2000 | Goldstein et al. | |
| 6,209,542 B1 | 4/2001 | Thornton et al. | |
| 6,374,824 B1 | 4/2002 | Thornton et al. | |
| 6,405,729 B1 * | 6/2002 | Thornton | A61F 5/566 128/206.29 |
| 6,464,924 B1 | 10/2002 | Thornton et al. | |
| 6,571,798 B1 | 6/2003 | Thornton et al. | |
| 7,677,889 B2 | 3/2010 | Thornton et al. | |
| 8,020,276 B2 | 9/2011 | Thornton et al. | |
| 8,236,216 B2 | 8/2012 | Thornton et al. | |
| 8,375,944 B2 | 2/2013 | Kwok | |

(Continued)

FOREIGN PATENT DOCUMENTS

WO    WO-0013751 A1 *   3/2000   ........ A61M 16/0666

OTHER PUBLICATIONS

"Types of Oral Appliances," an overview of types of oral appliances given to patients by Northview Dental (www.northviewdental.net) at least as early as Aug. 2016 (3 pages).

*Primary Examiner* — Joseph D. Boecker
(74) *Attorney, Agent, or Firm* — Pauly, DeVries Smith & Deffner LLC

(57) ABSTRACT

A strapless CPAP mask system is disclosed. The system includes a CPAP mask, a retainer attached to the CPAP mask, an oral appliance including a stem, and a connector that connects the stem of the oral appliance to the retainer, thus releasably securing the oral appliance to the CPAP mask without the use of straps.

19 Claims, 11 Drawing Sheets

(56) References Cited

U.S. PATENT DOCUMENTS

| | | | |
|---|---|---|---|
| 8,607,796 B2 | 12/2013 | Thornton et al. | |
| 2004/0065328 A1 | 4/2004 | Amarasinghe et al. | |
| 2005/0199240 A1 | 9/2005 | Hall et al. | |
| 2006/0231101 A1* | 10/2006 | Cannon | A61M 16/0488 128/206.29 |
| 2008/0053446 A1 | 3/2008 | Sleeper et al. | |
| 2008/0149105 A1* | 6/2008 | Matula | A61M 16/06 128/206.29 |
| 2012/0103343 A1* | 5/2012 | Goldstein | A61M 16/0666 128/207.18 |
| 2012/0298110 A1 | 11/2012 | Thornton et al. | |
| 2014/0053852 A1* | 2/2014 | Thornton | A61F 5/566 128/862 |
| 2014/0290668 A1* | 10/2014 | Thornton | A61F 5/566 128/848 |
| 2019/0240435 A1* | 8/2019 | Anderson | A61M 16/1045 |

* cited by examiner

CPAP MASK ATTACHMENT SYSTEM

CROSS-REFERENCE TO RELATED APPLICATIONS

This application claims priority from U.S. Provisional Patent Application No. 62/329,051, filed Apr. 28, 2016, the entirety of which is herein incorporated by reference.

BACKGROUND

Sleep apnea is a medical condition that affects the sleep of many people. Physicians use a device called a continuous positive airway pressure (CPAP) machine to treat sleep apnea. A CPAP machine requires a patient to wear a mask over the face while sleeping. Some CPAP masks cover only the patient's nose, while others cover both the patient's mouth and nose. Straps that attach the mask to the patient's head create marks on the head and face, and can even cause changes in tissue, leaving patients with puffy eyes, enlarged nasal openings, or indentations in the forehead.

SUMMARY

A CPAP mask attachment system is disclosed. The system includes a CPAP mask having a first attachment site and a second attachment site, an oral appliance including a stem, a retainer comprising a first wing and a second wing configured to connect to the CPAP mask at the first attachment site and the second attachment site, and a connector configured to releasably secure the stem to the retainer.

In another aspect, a system is disclosed that includes a stem configured to attach to an oral appliance, a retainer having a first wing and a second wing, the first wing and the second wing of the retainer being configured to attach the retainer to a CPAP mask, and a connector configured to releasably secure the stem to the retainer.

A method for fitting a device to a patient is also disclosed. The method includes positioning a CPAP mask on a desired location on the patient's face, attaching a retainer having a first wing and a second wing to the CPAP mask, and, while the patient is wearing an oral appliance having a protruding stem, orienting a connector to releasably attach the protruding stem to the retainer so as to secure the CPAP mask on the desired location on the patient's face.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense.

DETAILED DESCRIPTION

Figure 1:
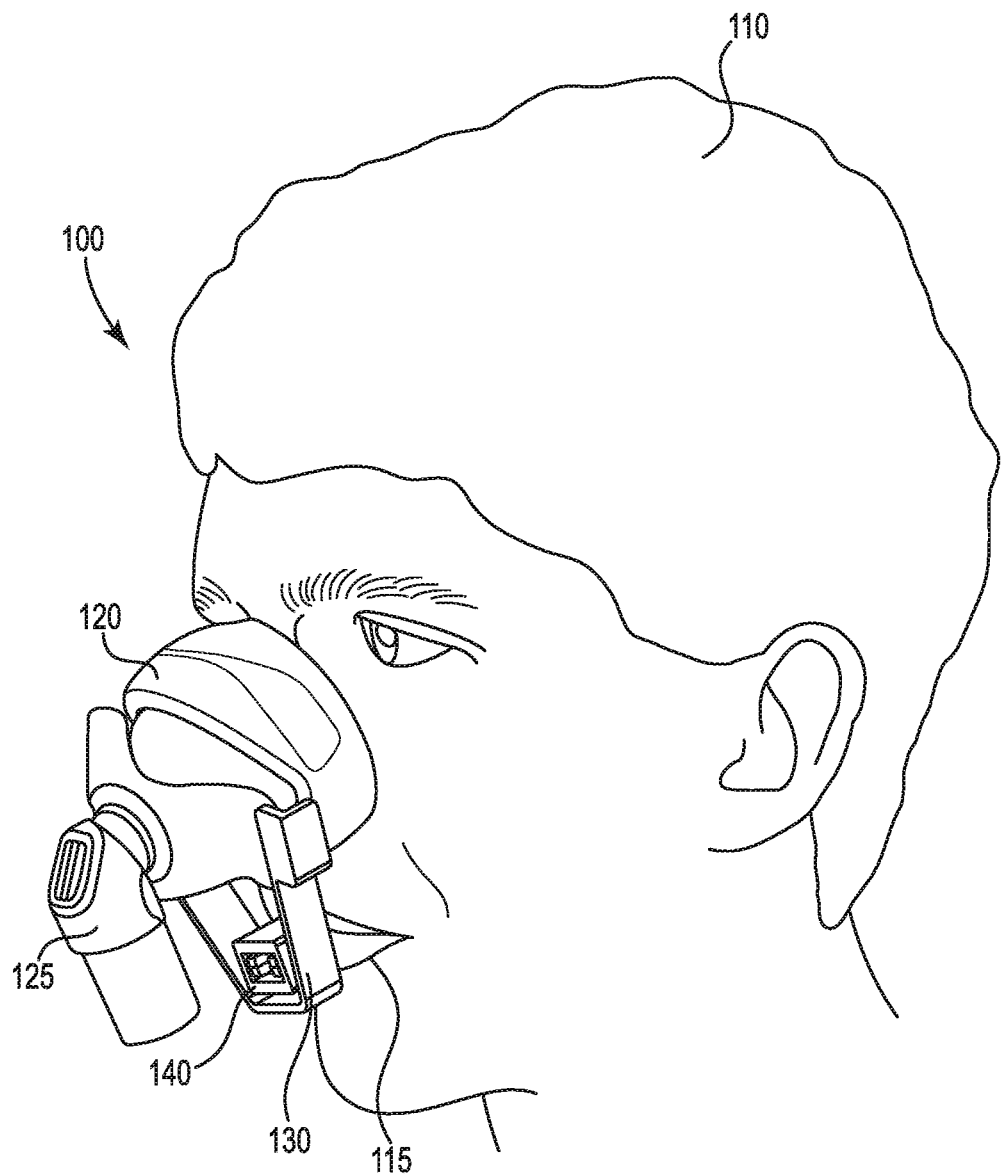
FIG. 1 is a perspective view of a patient wearing a CPAP mask attachment system of one embodiment.

A system for attachment of a continuous positive airway pressure (CPAP) mask is disclosed. The system will attach a commercially available CPAP mask to a well-retained maxillary oral appliance, such as: plastic or acrylic mouth guards, splints, or upper appliances that are a part of a mandibular advancement appliance. The disclosed system offers a rigid connector that will quickly disconnect and reconnect the oral appliance and the CPAP mask. The system allows a CPAP mask to be used without a strap. Because the system is strapless, it reduces the problems associated with conventional CPAP masks.

In some examples, a maxillary oral appliance is formed at a commercial dental lab, or chairside by a dentist. The oral appliance is custom-fitted and retentive to the patient's dental arch form. The system includes a stem protruding from the oral appliance. The stem can be a plastic or other suitable material that can be shaped and attached to the oral appliance. The stem may include one or more tabs or stops.

A connector is configured to receive the stem in a recess. In some examples, the stem is coupled to the connector with a friction fit. The tabs or stops may be suitably situated on the stem of the oral appliance to improve the friction fit. In some examples, the system can be configured such that the friction fit provides enough security to allow maximum pressure on the CPAP mask while still allowing easy decoupling of the stem and the connector without having to remove the oral appliance from the patient's mouth.

The system includes a retainer arch that is attached to or integrated with the connector. The retainer arch, which can consist of a flexible material, is coupled to a commercially available CPAP mask. The retainer arch can have two wings that attach to the right and left sides of the CPAP mask. The retainer arch retains the mask on the patient's face during use, eliminating the need for additional straps pressing against the patient's face or head.

The oral appliance, connector, retainer arch, and CPAP mask are assembled and properly positioned for the patient's comfort. The dentist may cement one or more of the pieces—the connector, retainer arch, and CPAP mask—to customize the fit for the patient; other methods of bonding or connecting other than cement can be used. In some examples, light-cured cement can be used. In other examples, the retainer arch can instead clip on to the CPAP mask.

In some examples, the oral appliance, which is a maxillary oral appliance, is formed using an impression of the patient's dental arch. A dentist can adjust the appliance for proper fit and occlusion. The stem is then attached to the appliance. The oral appliance, along with the connector, retainer arch, and CPAP mask, can then be fitted for the patient.

In some examples, fitting the system includes inserting the oral appliance into the patient's mouth, inserting the stem into the connector, and causing the stem and the connector to be secured with a friction fit. The CPAP mask is held on the patient's face by the patient, allowing the two wings of the retainer arch to be attached to the left and right sides of the mask. The wings of the retainer arch can be made specific to commercial masks for the ease of cementing. The connector is then bonded to the retainer arch.

After being fitted, the CPAP mask is rigidly retained on the patient's face during use. To use the system, the patient first inserts the oral appliance into the mouth and then couples the stem and the connector with a friction fit. Inserting the connector into the stem causes the mask to be positioned at the appropriate place against the patient's face. The friction fit at the interface between the stem and the connector allows the mask to be quickly and easily removed, even when the oral appliance is inserted in the patient's mouth, by pulling the stem out of the connector.

In practice, the CPAP mask attachment system can be fitted in two visits to a dental professional's office. A number of different CPAP masks can be converted to the strapless CPAP mask attachment system. In the first visit, the patient brings the patient's own approved CPAP mask to the dental office. The dental professional takes an impression of the patient's dental arch. In some examples, the dental professional sends the impression to a laboratory, where the oral appliance is created and a stem is attached the oral appliance. Alternatively, if the patient already has an oral appliance, that appliance can be used. Next, the patient holds the CPAP mask in a comfortable position on the face so that no air can leak out of the seal of the mass during use. The retainer arch is then adjusted in an appropriate position both to the front of the CPAP mask, and aligned with the bottom of the patient's mouth so that eventually the stem can be placed on the oral appliance and connected to the retainer. The dental professional then bonds the retainer arch to the CPAP mask in the customized position.

In alternative examples, the CPAP mask and the retainer can be integrally formed by the mask manufacturer, making the steps of bonding the first and second wings of the retainer arch to the CPAP mask unnecessary.

In a second visit to the dental office, the oral appliance is adjusted for anterior muscle deprogramming, and for comfort on the cuspids and/or central incisors. The stem of the oral appliance is inserted into a connector. The stem and the connector couple with a friction fit. The oral appliance is then inserted into the patient's mouth with the connector and stem protruding from the patient's mouth. Patient again holds the CPAP mask in the appropriate location on the patient's face. The connector will protrude through the bottom of the retainer arch. The dental professional then cements the connector to the retainer arch in such a way that the CPAP mask, the retainer, and the oral appliance are in a rigid formation and do not move in relation to one another. At this point, the connector can be removed from the stem. The CPAP mask, retainer, and connector are now attached together. In some cases, these pieces can be attached more securely by finishing the fitting with additional adhesive or cement.

To ensure proper placement, the oral appliance and stem are again inserted into the patient's mouth, and the connector is coupled with the stem. If the mask is properly fitted, the oral appliance, connector, retainer, and CPAP mask will be rigidly held in place, with no leaks between the mask and the patient's skin.

Figure 2:
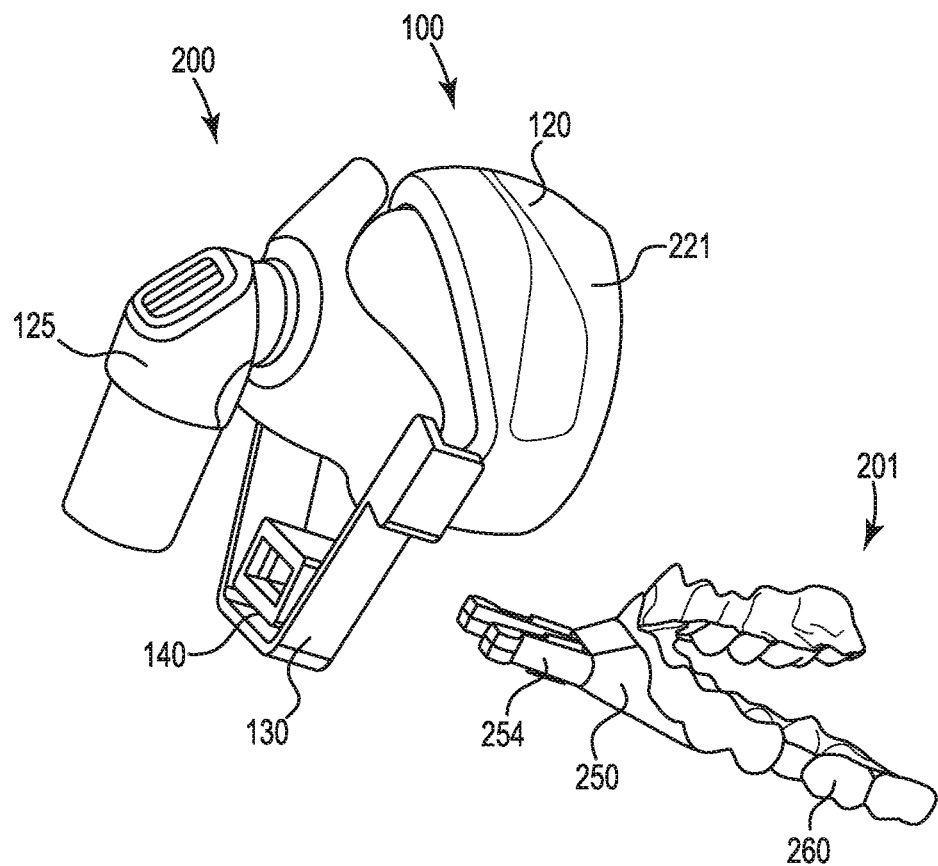
FIG. 2 is a side view of the system according to the embodiment of FIG. 1.
Figure 3:
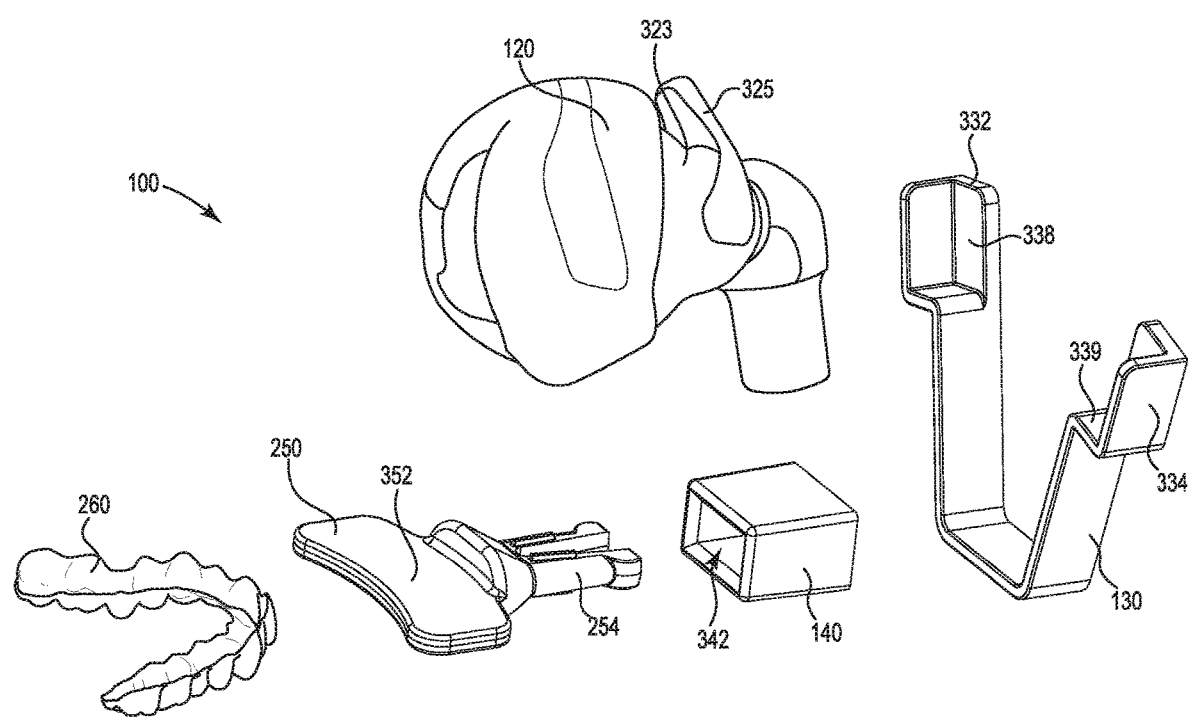
FIG. 3 is an exploded view of the system according to the embodiment of FIG. 1.

Turning to the drawings, FIGS. 1-3 show different views of the CPAP mask attachment system according to some examples. FIG. 1 is a perspective view of a patient wearing a CPAP mask attachment system. As shown in FIG. 1, the system is configured to securely engage the CPAP mask 120 to the patient's face without the use of a strap. The system 100 includes a CPAP mask 120 having a nozzle 125 for delivering treatment to the patient 110. A hose (not shown) attaches the nozzle 125 of the CPAP mask 120 to a machine that delivers continuous positive airway pressure to the patient. The CPAP mask 120 in this example covers the patient's nose, while the patient's mouth 115 is not covered by the mask. An oral appliance (shown in FIG. 2) fits in the patient 110's mouth. The oral appliance connects to a retainer 130 via a connector 140. The retainer 130 is attached to the CPAP mask 120. As will be discussed further below, the CPAP mask 120 can be easily removed from the face without removing the oral appliance.

As shown more clearly in FIG. 2, the system 100 is provided in two separate pieces. The first piece 200 includes the CPAP mask 120, retainer 130 attached to the CPAP mask 120, and connector 140 attached to the retainer 130. The second piece 201 includes an oral appliance 260 and a stem 250 protruding from the oral appliance 260. FIG. 3 shows an exploded view of the first piece 200 and the second piece 201 comprising their respective sub-elements. The first piece 200 is configured to be placed against the patient 110's face. The second piece 201 is configured to fit inside patient 110's mouth. The first piece 200 and the second piece 201 are configured to retain the CPAP mask 120 in place without the use of additional straps so that CPAP therapy can be comfortably delivered to the patient 110.

When the patient 110 wears the second piece 201 in the mouth and the first piece 200 is connected to the second piece 201, the CPAP mask 120 is rigidly retained on the patient's face. This is made possible because the upper dental arch does not move in relation to the rest of the skull. The first piece 200 is configured to connect with the second piece 201 using a stem inserted into a connector recess. The system 100 is configured such that when the oral appliance 260 is in patient 110's mouth, sliding the stem 250 into the connector 140 causes the CPAP mask 120 to be secured to the patient 110's face.

The Oral Appliance and Associated Parts

Figure 6:
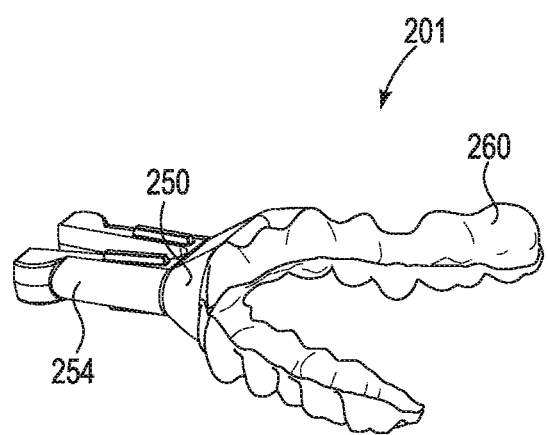
FIG. 6 is a perspective view of an oral appliance attached to a stem.

With reference to FIGS. 2 and 3, the second piece 201 of system 100 includes oral appliance 260. The oral appliance 260 can be a maxillary oral appliance that is fitted to the patient 110's dental arch by a professional. In some examples, the oral appliance 260 is made of a rigid material. In some examples, the oral appliance 260 is a mandibular advancement device that is configured to move the lower jaw forward when worn by the patient. These devices treat snoring and obstructive sleep apnea. Such a device is worn during sleep to open the patient's airway. In some examples, the oral appliance 260 can be any rigid oral appliance that conforms to the patient 110's dental arch, such as an anterior deprogrammer, stabilization splint, or mouth guard. FIG. 6 provides an additional perspective view of oral appliance 260 attached to stem 250.

In some examples, the oral appliance 260 is fitted to the patient 110 by a qualified dental professional. This is because improperly fitted oral appliances can cause temporomandibular joint dysfunction (TMJ) and occlusion problems, which can cause pain in the jaw and associated muscles. A dental professional can provide the proper fit to avoid these potential problems.

The second piece 201 also includes a stem 250 that is attached to the oral appliance 260. The stem 250, in combination with the connector 140, couples the CPAP mask 120 of the first piece 200 and the oral appliance 260 of the second piece 201. In some examples, the stem 250 is rigidly attached to the bottom portion of the oral appliance 260, such as with a cement or other substance to bond the stem 250 to the oral appliance 260. In alternative examples, the oral appliance 260 and the stem 250 could be a single construction instead of two separate sub-elements.

The stem 250 includes at least one prong 254 that protrudes from the stem 250. The prong 254 is configured to releasably attached to the connector 140. In some examples, the outer surface of the stem 250 and the prong 254 is configured to provide a friction fit between the stem 250 and the connector 140. The stem 250 is made of an appropriately rigid material, such as polycarbonate. In some examples, the material from which the stem 250 is made can be slightly flexible while still being rigid. In some examples, the body of the stem 250 can be made from a different material than the prong 254. The stem 250 can be made by processes such as, e.g., molding, 3D printing, or any suitable manufacturing processes.

Figure 7:
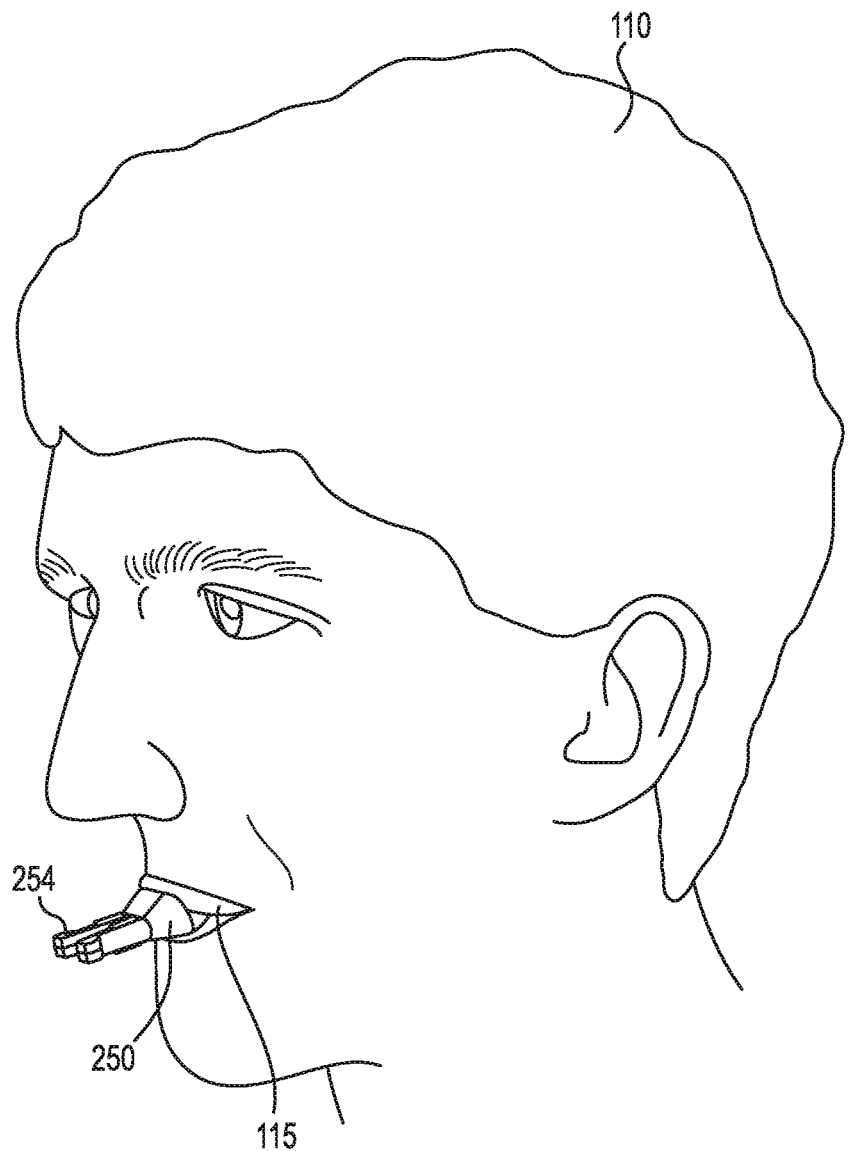
FIG. 7 is a perspective view of a patient wearing the oral appliance with the stem.

FIG. 7 is a perspective view of patient 110 wearing the oral appliance 260 with the prong 254 protruding from the mouth 115. In the illustrated example, the stem 250 is cemented to the bottom of the oral appliance 260, which places the prong 254 approximately perpendicular to the patient 110's front teeth. However, this positioning will be adjusted to suit a particular patient's unique anatomy. In some embodiments, this positioning is performed by a dental professional. The location of the stem 250 and the prong 254 is configured such that the stem 250 protrudes comfortably from between the patient 110's lips. If the stem 250 is placed too high with respect to the patient 110's lips, the upper lip will be pushed uncomfortably high. If the stem 250 is located too low with respect to the patient 110's lips, the lower lip will be pushed uncomfortably low.

The CPAP Mask and Associated Parts

Referring again to FIGS. 2 and 3, in some examples, the CPAP mask 120 is a nasal CPAP mask. These masks are compact and lightweight. Nasal masks are designed to be placed over the nose, and do not cover the mouth. Specifically, nasal masks enclose the bridge of the nose, the cheekbones, and the upper lip, while the mouth is not enclosed.

In alternative examples, the CPAP mask 120 can be a different type of CPAP mask that is adaptable to the present disclosure, such as nasal pillows. Nasal pillows differ from nasal masks in that nasal pillows direct airflow into the nasal passages. Nasal pillows do not engage the bridge of the nose or the cheekbones. Instead, nasal pillows press against the nostrils, forming a seal around only the nostril openings. Thus, nasal pillows require a force to be directed against the nostril openings. Not all patients find nasal pillows comfortable; some patients prefer a configuration in which the CPAP mask rests against the bridge of the nose, the cheekbones, and the upper lip. Nasal masks are adapted to be able to apply a force to the right of the patient's nose and to the left of the patient's nose, distributing the force across a wider surface. In contrast, the force of the nasal pillow is concentrated on the nostrils.

In alternative embodiments, the CPAP mask can be a full-face CPAP mask. Other examples will be apparent to those of ordinary skill in the art.

The CPAP mask 120 has a seal 221 that sits against the face. The seal 221 prevents air leakage. In the embodiment of FIG. 2, the seal 221 presses against the bridge of the nose, the cheekbones, and the upper lip of patient 110. The seal 221 can be made of a soft silicone material, or a similar material that is comfortable against the skin. Soft silicone material allows the seal 221 to conform to the face of the patient 110 such that there are no gaps between the mask 120 and the skin of the patient 110 for air to leak through. A typical nasal CPAP mask also has an air chamber 323 that covers the patient 110's nose, and a rigid frame 325.

Figure 4:
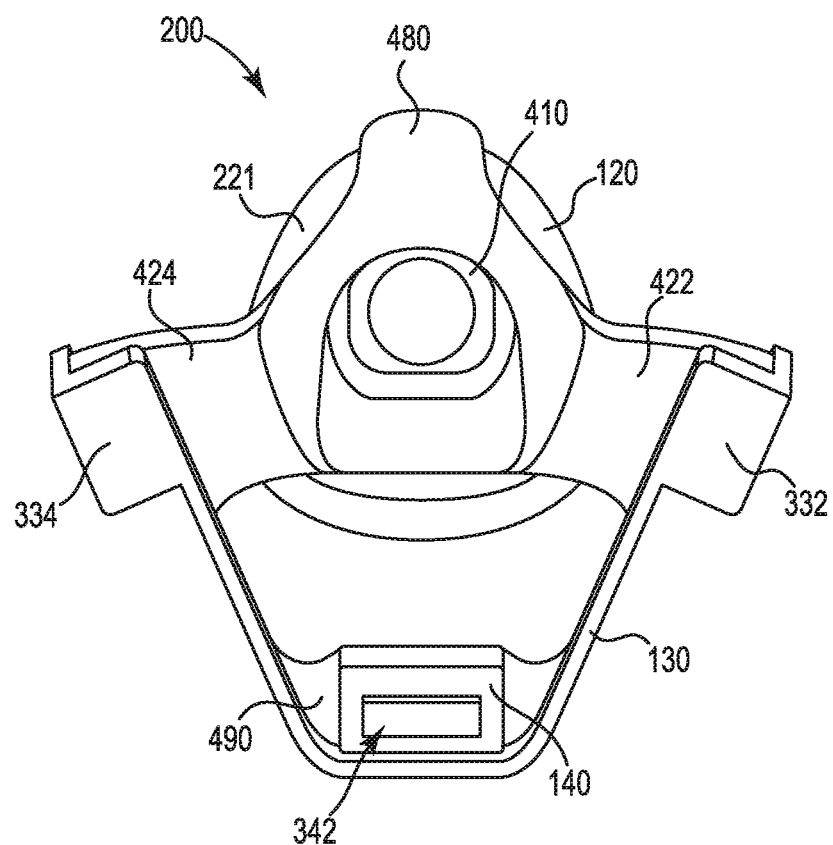
FIG. 4 is a front view of a CPAP mask attached to a retainer according to the embodiment of FIG. 1.
Figure 5:
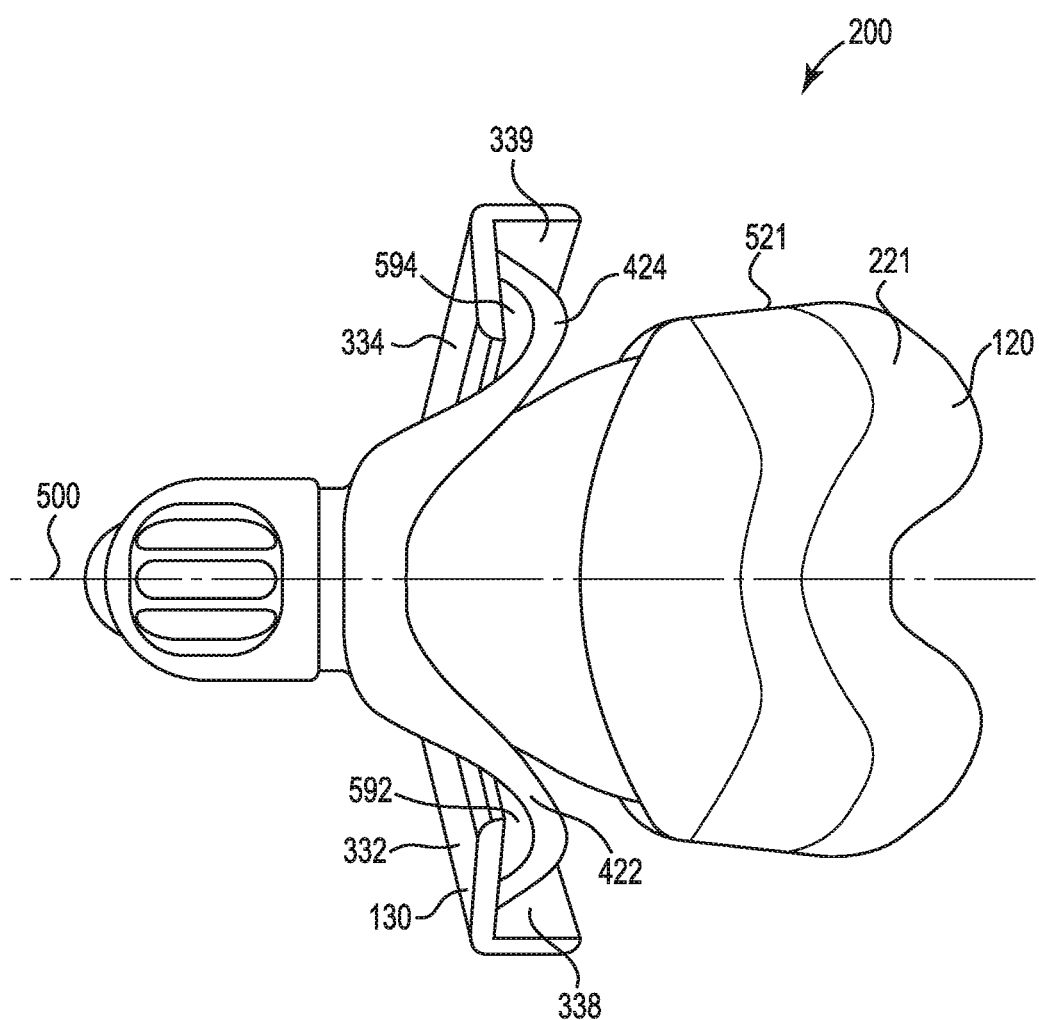
FIG. 5 is a top view of the CPAP mask attached to the retainer according to the embodiment of FIG. 1.

FIGS. 4 and 5 provide additional views of the first piece 200, which includes the CPAP mask 120, the retainer 130, and the connector 140. The retainer 130 is attached to the CPAP mask 120 at the right and left sides of the mask 120. In use, the retainer 130 provides a retaining force to the CPAP mask 120 both to the right side of the user's face and to the left side of the user's face. In some examples, the CPAP mask 120 and retainer 130 are bonded together in such a way that they are immovable with respect to one another. For example, the retainer 130 can be bonded to the mask 120 with a cement or other suitable permanent attachment material. In alternative examples, the retainer 130 can releasably attach to the CPAP mask 120, for example with a clip. In these alternative examples, the clip that attaches the retainer 130 to the CPAP mask 120 rigidly holds the retainer 130 and the CPAP mask 120 such that they do not move in relation to one another.

In some examples, the retainer 130 comprises a first wing 332 and a second wing 334 that are configured to attach to the right and left sides of the CPAP mask 120. The first and second wings 332, 334 are configured to sit against the front of the CPAP mask 120. In some examples, recesses 338, 339 connect to the front of the CPAP mask 120. In some examples, the wings can include recesses that are molded to the shape of the CPAP mask 120. In alternative examples, the recesses 338, 339 can have a generic shape that can fit on many different masks made by different mask manufacturers.

FIG. 4 shows the first piece 200 with the nozzle 125 removed to provide a better view of the first piece 200; a passageway 410 provides a path for air to flow from the nozzle 125 into the inside of the CPAP mask 120. In the example of FIG. 4, the seal 221 covers the patient 110's nose, preventing air from leaking out of the CPAP mask.

The CPAP mask 120 has attachment sites 422, 424. The first attachment site 422 attaches to the first wing 332 of the retainer 130, and the second attachment site 424 attaches to the second wing 334 of the retainer 130. In some examples, the first attachment site 422 on the CPAP mask 120 is located on the outer edge of the mask 120.

In the example of FIG. 5, the attachment site 424 is located at least about the same distance from the centerline 500 of the mask 120 as the outer edge 521 of the seal 221. In this example, the first attachment site 422 is distal to one side of the patient 110's nose and the second attachment site 424 is distal to the opposite side of the user's nose when the CPAP mask 120 is placed on the user's face. Stated differently, the width of the retainer 130 measured from the first wing 332 to the second wing 334 is as wide or wider than the width of the seal 221.

In some examples, the attachment site 422 and the first wing 332 are formed such that the shape of the recess 338 conforms to the shape of the surface of attachment site 422. Similarly, in such an embodiment the attachment site 424 and the first wing 332 are formed such that the shape of the recess 339 conforms to the shape of the surface of attachment site 424.

In some examples, such as that in FIG. 5, the recess 338 is not perfectly fitted to the shape of attachment site 422 of the CPAP mask 120. In this case, an interfacing piece 592 is placed between the attachment site 422 and the recess 338 of the second wing 334 so that no gaps are present between the CPAP mask 120 and the retainer 130. The interfacing piece 592 is shaped to conform to the shape of the first recess 338 and the first attachment site 422 on the CPAP mask. Similarly, a second interfacing piece 594 is shaped to conform to the shape of the second recess 339 and the second attachment site 424 on the CPAP mask 120.

In some examples, the first interfacing piece 592 and the second interfacing piece 594 are pre-formed to match the shape of the first attachment site 422 and the second attachment site 424 respectively.

In other examples, the interfacing pieces 592, 594 can be made of a malleable material that conforms to the shape of the attachment sites and recesses. For example, a malleable thermoplastic material is heated and then placed inside of the recesses 338 and 339. Then the CPAP mask 120 is positioned against the retainer 130 so that the first attachment site 422 presses against the thermoplastic material inside the recess 338 and the second attachment site 424 presses against the thermoplastic material inside of the recess 339. The pressure between the CPAP mask 120 and the retainer 130 causes the thermoplastic material to mold into a shape that conforms to both the attachment sites 422, 424 and the first and second wings 332, 334.

In some examples, the interfacing pieces 592, 594 are bonded to the first and second attachment sites 422, 424 and the first and second recess 338, 339 using an adhesive. For example, cyanoacrylates can be used as the adhesive. In alternative examples, the interfacing pieces 592, 594 themselves may be made of a material that is both malleable and adhesive.

Referring again to FIGS. 2 and 4, first piece 200 also includes a connector 140 that is attached to the retainer 130. The connector 140 includes a recess 342 that is configured to couple with the prong 254. In some examples, the connector 140 is bonded to the retainer 130. In the example of FIGS. 1-5, the connector 140 is bonded to the retainer 130 using a cement 490 shown in FIG. 4. The cement 490 is adhesive, and adheres to both the retainer 130 and the connector 140, bonding the two pieces together. Other methods of bonding the retainer 130 with the connector 140 will be apparent to of those of ordinary skill in the art. In alternative examples, the retainer 130 and the connector 140 could be integrally formed from a single piece of material. Similarly, in alternative examples the entire first piece 200 including the mask 120, the retainer 130, and the connector 140 can be integrally formed from a single piece of material.

The Connector and Stem

Figure 8:
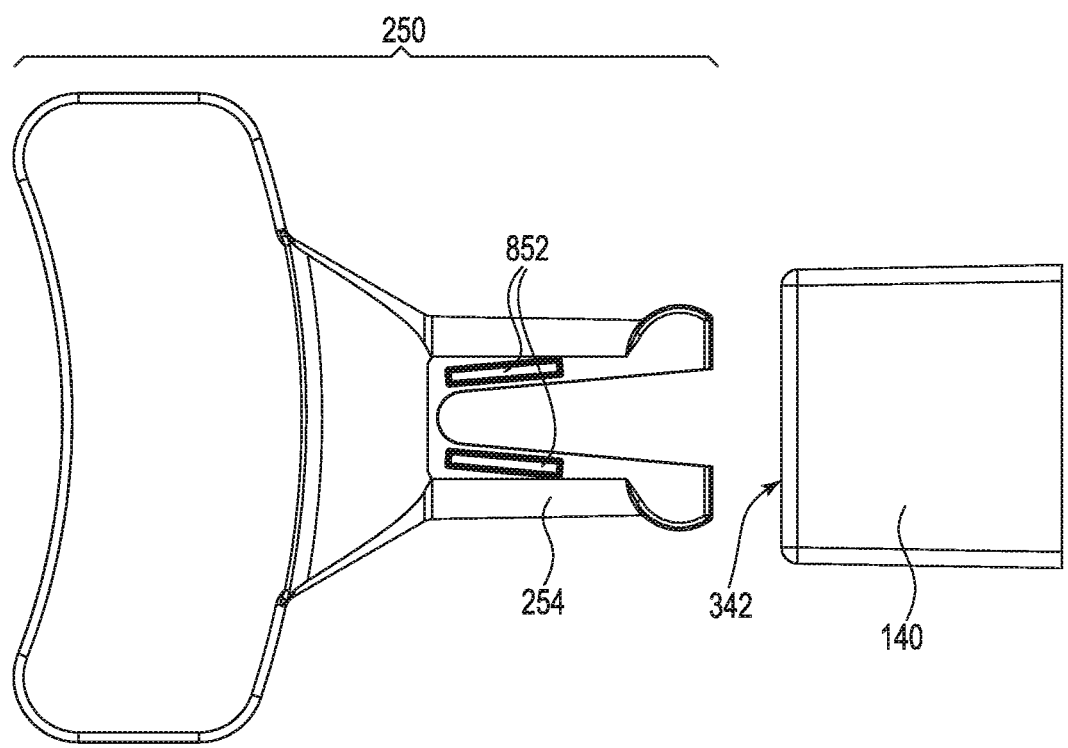
FIG. 8 is a top view of a stem and a connector according to an embodiment.
Figure 9:
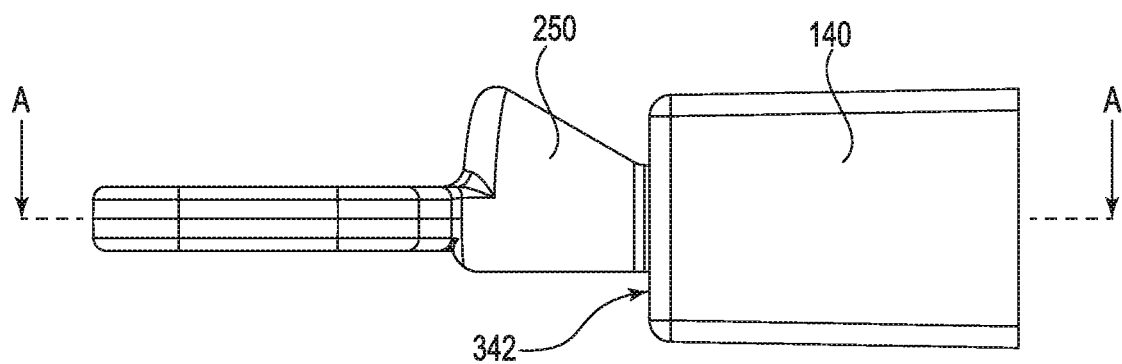
FIG. 9 is a side view of the stem engaged with the connector.
Figure 10:
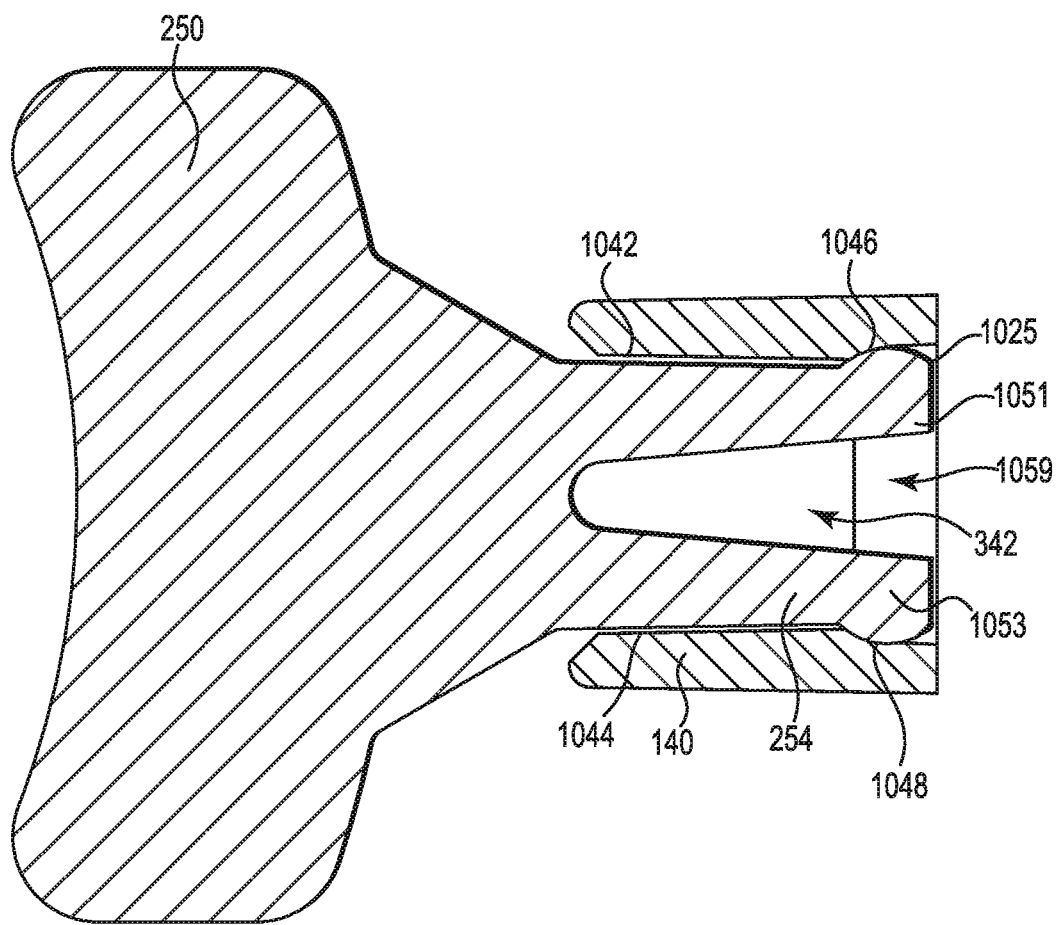
FIG. 10 is a cross-sectional view of the stem engaged with the connector.

FIGS. 8-10 show the interconnection of the stem 250 and the connector 140. Referring to FIG. 8, the stem 250 comprises at least one prong 254. The prong 254 is configured to be inserted into recess 342 of the connector 140. As detailed with respect to FIG. 2, the stem 250 is part of the second piece 201, and the connector 140 is part of the first piece 200. In use, when the prong 254 of stem 250 is inserted into the recess 342 of the connector 140, the first piece 200 and the second piece 201 interlock, and the entire system 100 is retained in a rigid formation. That is, each of the components do not move in relation to each other when the stem 250 is inserted into the connector 140. Furthermore, when the patient 110 has the second piece 201 positioned in the mouth, as shown in FIG. 7, sliding the connector 140 of the first piece 200 over the stem 250 of the second piece 201 causes the CPAP mask 120 to be positioned onto the face of patient 110 such that the CPAP mask 120 is releasably secured to the face.

In some examples, the connector 140 and the stem 250 releasably engage together with a friction fit. In some examples, the stem 250 comprises a raised section 852, the connector 140 comprises a top wall and a bottom wall, and the raised section 852 is configured to slidably engage with one of the top wall and the and bottom wall of the connector 140 to provide a friction fit. In the example of FIG. 8, the prong 254 includes one or more raised sections 852 that provide friction against the inside surfaces of the recess 342. The raised sections 852 are elongated protrusions on the top of the prong 254. In addition to providing friction, the raised sections 852 provide stability. FIG. 9 shows the stem 250 inserted into the recess 342 of connector 140. The raised sections 852 (not in view in FIG. 9), prevent the stem 250 from moving up and down in the connector recess 342. A rigid connection, that is, a connection that prevents excess motion between the stem 250 and the connector 140, improves the stability of the CPAP mask 120 against the face of the patient 110.

FIG. 10 is a cross-sectional view of the stem 250 and the connector 140 taken along the line A-A of FIG. 9. In the example of FIG. 10, the stem 250 has a forked prong 254 defining a gap 1059 between two tines 1051, 1053. The tines 1051, 1053 slidably engage with the sidewalls 1042, 1044 of the connector recess 342. In some examples, the tine 1051 may include a curvature 1025 at the end of the tine 1051. The curvature 1025 helps to ease the stem 250 into the connector recess 342. The tines 1051, 1053 are pushed together slightly when the prong 254 is initially inserted into the recess 342, causing the gap 1059 to narrow. This narrowing of the gap 1059 causes the prong 254 to exert outward force on the sidewalls 1042, 1044 of the connector 140.

In some examples, the connector 140 also has recesses 1046, 1048 at the end of the connector 140 opposite the stem 250. The recesses 1046, 1048 together provide a space inside the recess 342 that is wider than the space between the sidewalls 1042, 1044. In the example of FIG. 10, the tine 1051 sits in the recess 1046 and the tine 1053 sits in the recess 1048. The recesses 1046, 1048 provide a mechanical barrier that must be overcome in order to disengage the stem 250 from the connector 140. In practice, to disengage the stem 250 from the connector 140, sufficient force must be exerted on the stem 205 to overcome the friction fit between the tines 1051, 1053 and the sidewalls 1042, 1044. In examples in which the connector 140 has recesses 1046, 1048, sufficient force must also be applied to cause the tines 1051, 1053 to bend inward, narrowing the gap 1059 of the prong 254 so that prong 254 can slide out of the connector 140.

Method of Fitting a CPAP Mask to a Patient

Figure 11:
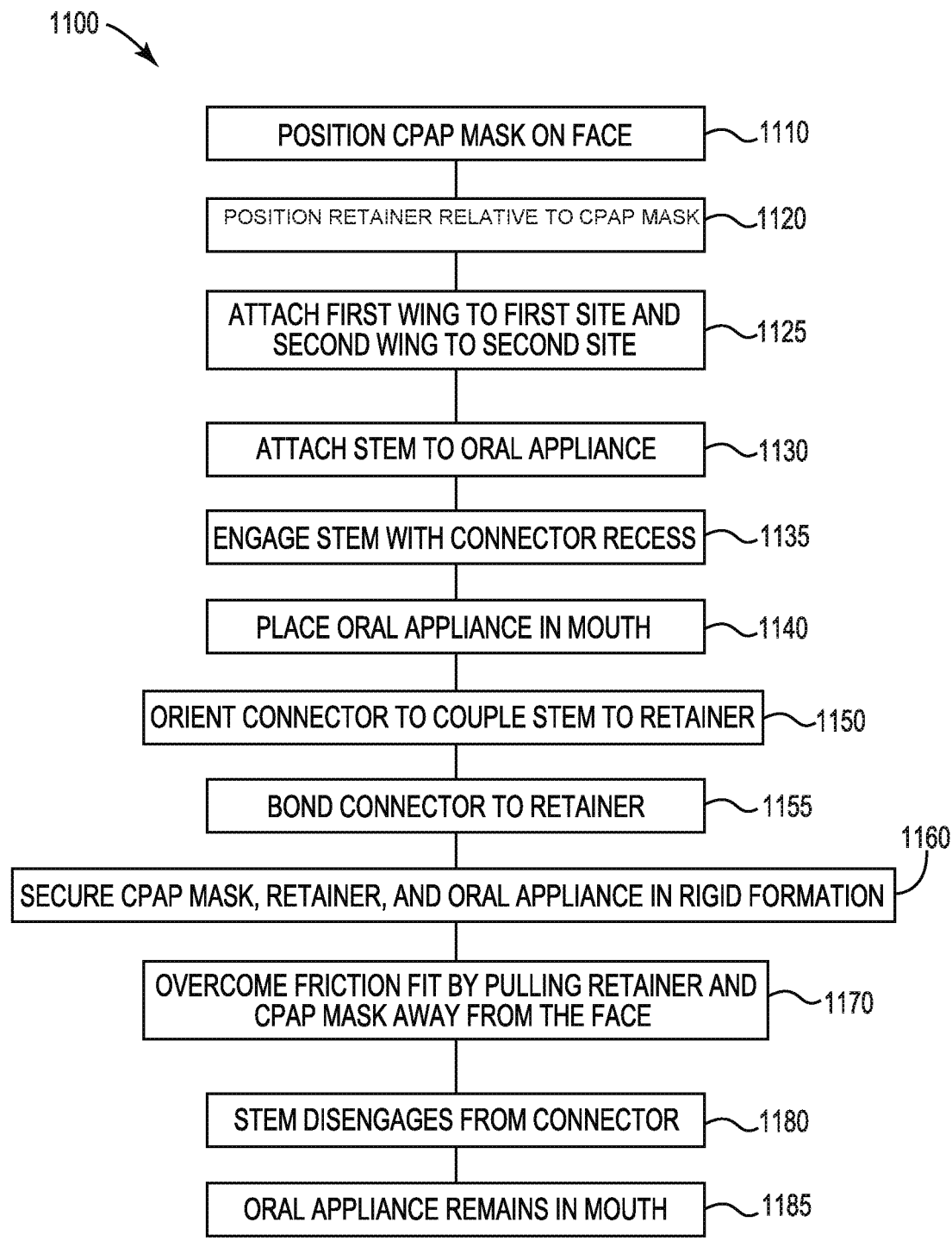
FIG. 11 is a flow chart for a method of fitting a CPAP mask to a patient.

Turning to FIG. 11, a method 1100 is provided to fit a CPAP mask to a patient. The method 1100 is presented as a series of steps, however, these method steps do not need to be performed in the order presented. These steps may be performed in multiple combinations and orders. Not all steps must be performed.

In step 1110, the CPAP mask is positioned on a patient's face. In step 1120, a retainer is positioned relative to the to the CPAP mask. In this step, the relative position of the retainer and the CPAP mask are adjusted by a clinician, so that the bottom portion of the retainer is in front of the patient's bottom lip, and the CPAP mask is placed against the face such that no air can leak between the CPAP mask's seal and the face. In step 1125, the clinician attaches a first wing of the retainer to a first attachment site on the CPAP mask, and then attaches a second wing of the retainer to a second attachment site on the CPAP mask. In step 1130, an oral appliance is provided, and a stem is attached to the oral appliance. In step 1135, the stem is engaged with a recess of a connector. The oral appliance is inserted into the mouth at step 1140, and the connector is oriented to couple the stem to the retainer in a position that will allow the oral appliance to retain the CPAP mask on the face without the use of a strap. In step 1155, the connector is bonded to the retainer. In step 1160, the CPAP mask, retainer, and the oral appliance are secured in a rigid formation. To remove the CPAP mask from the patient's face while the oral appliance is inserted in the patient's mouth, at step 1170 the friction fit between the stem and the connector is overcome by pulling the retainer and the CPAP mask away from the patient's face. The force from pulling the retainer and mask away disengages the stem from the connector at step 1180. At step 1185, the CPAP mask is removed away from the patient's face while the oral appliance remains in the patient's mouth.

It should be noted that, as used in this specification and the appended claims, the singular forms include the plural unless the context clearly dictates otherwise. It should also be noted that the term "or" is generally employed in its sense including "and/or" unless the content clearly dictates otherwise.

All publications and patent applications referenced in this specification are herein incorporated by reference in their entirety.

While embodiments herein are susceptible to various modifications and alternative forms, specifics thereof have been shown by way of example and drawings. It should be understood, however, that the scope herein is not limited to the particular examples described. On the contrary, the intention is to cover modifications, equivalents, and alternatives falling within the spirit and scope herein.

What is claimed is:

1. A system comprising:
    a CPAP mask having a first attachment site and a second attachment site;
    an oral appliance including a stem;
    a retainer comprising a first wing and a second wing configured to connect to the CPAP mask at the first attachment site and the second attachment site, wherein the retainer is configured to secure the CPAP mask and the oral appliance in a rigid formation; and
    a connector configured to releasably secure the stem to the retainer.

2. The system of claim 1, wherein the first attachment site on the CPAP mask is distal to one side of a user's nose and the second attachment site on the CPAP mask is distal to an opposite side of the user's nose when the CPAP mask is placed on the user's face.

3. The system of claim 1, wherein the oral appliance and the retainer secure the CPAP mask against a patient's face without the use of a strap.

4. The system of claim 1, wherein the connector comprises a recess, and wherein the CPAP mask is releasably secured to a user's face when the stem is inserted into the recess of the connector.

5. A system comprising:
    a stem configured to attach to an oral appliance, wherein the stem comprises a forked portion defining a gap;
    a retainer having a first wing and a second wing, the first wing and the second wing of the retainer being configured to attach the retainer to a CPAP mask; and
    a connector configured to releasably secure the stem to the retainer, wherein the connector comprises a recess having side walls; and
    wherein the forked portion of the stem is configured to slidably engage with the side walls of the recess.

6. The system of claim 5 further comprising the CPAP mask attached to the first wing and the second wing of the retainer.

7. The system of claim 5, wherein the retainer is configured to provide retaining force to the CPAP mask both to the right side of a user's face and to the left side of the user's face.

8. The system of claim 5, wherein the stem comprises a raised section, the connector comprises a top wall and a bottom wall, and the raised section of the stem is configured to slidably engage with one of the top wall and the bottom wall to provide a friction fit.

9. The system of claim 6, wherein the system is configured to securely engage the CPAP mask to a user's face without the use of a strap.

10. The system of claim 6, wherein the connector, the retainer, and the CPAP mask are integrally formed.

11. The system of claim 6, wherein the first wing is attached to a first location on the CPAP mask with a first interfacing piece that is molded to the shape of the first wing and the first location on the CPAP mask, and the second wing is attached to a second location on the CPAP mask with a second interfacing piece that is molded to the shape of the second wing and the second location on the CPAP mask.

12. The system of claim 6, wherein the first wing and the second wing are releasably attached to the CPAP mask.

13. The system of claim 6 further comprising the oral appliance attached to the stem.

14. The system of claim 13, wherein the system is configured such that when the oral appliance is in a user's mouth, sliding the stem into the connector causes the CPAP mask to be secured to the user's face.

15. The system of claim 13, wherein the system is configured such that when a user wears the oral appliance in the mouth with the stem inserted into the connector and the CPAP mask on the user's face, pulling the CPAP mask away from the user's face overcomes a friction fit between the stem and the connector, allowing the stem and the oral appliance to be released from the connector and the CPAP mask.

16. A method for fitting a device to a patient, the method comprising:
    positioning a CPAP mask on a desired location on the patient's face;
    attaching a retainer having a first wing and a second wing to the CPAP mask; and
    while the patient is wearing an oral appliance having a protruding stem, orienting a connector to releasably attach the protruding stem to the retainer so as to secure the CPAP mask on the desired location on the patient's face; and
    bonding the connector and the retainer such that the CPAP mask, the oral appliance, and the retainer are secured in a rigid formation.

17. The method of claim 16, wherein the protruding stem releasably engages the connector with a friction fit.

18. A system comprising:
    a stem configured to attach to an oral appliance, wherein the stem comprises a raised section;
    a retainer having a first wing and a second wing, the first wing and the second wing of the retainer being configured to attach the retainer to a CPAP mask; and a connector configured to releasably secure the stem to the retainer, wherein the connector comprises a top wall and a bottom wall, and wherein the raised section of the stem is configured to slidably engage with one of the top wall and the bottom wall to provide a friction fit.

19. A system comprising:

a CPAP mask;

a stem configured to attach to an oral appliance;

a retainer having a first wing and a second wing, the first wing and the second wing of the retainer being configured to attach the retainer to the CPAP mask; and a connector configured to releasably secure the stem to the retainer; and wherein the first wing is attached to a first location on the CPAP mask with a first interfacing piece that is molded to the shape of the first wing and the first location on the CPAP mask, and the second wing is attached to a second location on the CPAP mask with a second interfacing piece that is molded to the shape of the second wing and the second location on the CPAP mask.

* * * * *